(12) United States Patent
Delnevo (10) Patent No.: US 11,596,782 B2
(45) Date of Patent: Mar. 7, 2023

(54) HOLDER FOR A CURVED DUCT PORTION

(71) Applicant: ALLMED MEDICAL CARE HOLDINGS LIMITED, London (GB)

(72) Inventor: Annalisa Delnevo, London (GB)

(73) Assignee: ALLMED MEDICAL CARE HOLDINGS LIMITED, London (GB)

( * ) Notice: Subject to any disclaimer, the term of this patent is extended or adjusted under 35 U.S.C. 154(b) by 323 days.

(21) Appl. No.: 16/620,677

(22) PCT Filed: Jun. 8, 2018

(86) PCT No.: PCT/IB2018/054156
§ 371 (c)(1),
(2) Date: Dec. 9, 2019

(87) PCT Pub. No.: WO2018/225027
PCT Pub. Date: Dec. 13, 2018

(65) Prior Publication Data
US 2020/0147281 A1    May 14, 2020

(30) Foreign Application Priority Data
Jun. 9, 2017   (IT) .................. 102017000064361

(51) Int. Cl.
*A61M 1/10*    (2006.01)
*F04B 43/12*    (2006.01)
(Continued)

(52) U.S. Cl.
CPC ........ *A61M 60/113* (2021.01); *A61M 60/109* (2021.01); *A61M 60/279* (2021.01);
(Continued)

(58) Field of Classification Search
CPC .. A61M 60/113; A61M 60/50; A61M 1/3621; A61M 2205/3334; F04B 43/1253; F04B 43/0072
See application file for complete search history.

(56) References Cited

U.S. PATENT DOCUMENTS 4,545,744 A    10/1985  Weber et al.
6,494,692 B1   12/2002  Green
(Continued)

FOREIGN PATENT DOCUMENTS

WO    WO2005088132 A1    9/2005
WO    WO-2010092729 A1 *  8/2010   .......... F04B 43/1261

OTHER PUBLICATIONS

Itoh, Yoichi, 'Tube Pump', Aug. 19, 2010.*

*Primary Examiner* — Adam Marcetich
*Assistant Examiner* — Rachel O'Connell
(74) *Attorney, Agent, or Firm* — Aslan Law, P.C.

(57) ABSTRACT

A holder for a curved duct portion of a tube pump. The holder includes a supply-side connector which includes a first cavity and a first plate connected together, the first cavity being adapted for receiving an end of the curved duct portion, and a discharge-side connector including a second cavity and a second plate connected together, the second cavity being adapted for receiving another end of the curved duct portion, where the connectors are movable the one with respect to the other between a storage configuration, in which the supply-side connector is positioned away to the discharge-side connector, and an operating configuration, in which the supply-side connector is close to the discharge-side connector and in which the first and second plate are engaged together substantially on a same plane.

1 Claim, 6 Drawing Sheets

(51) Int. Cl.
*A61M 1/36* (2006.01)
*F04B 43/00* (2006.01)
*A61M 60/113* (2021.01)
*A61M 60/462* (2021.01)
*A61M 60/279* (2021.01)
*A61M 60/109* (2021.01)

(52) U.S. Cl.
CPC ....... *A61M 60/462* (2021.01); *F04B 43/1253* (2013.01); *A61M 1/3621* (2013.01); *A61M 2205/3334* (2013.01); *F04B 43/0072* (2013.01)

(56) References Cited

U.S. PATENT DOCUMENTS

| | | | |
|---|---|---|---|
| 2014/0012176 A1* | 1/2014 | Schaefer | A61M 1/3621 604/6.16 |
| 2017/0028117 A1* | 2/2017 | Mochizuki | F04B 43/1253 |
| 2017/0096993 A1* | 4/2017 | Arashi | F04B 43/08 |
| 2017/0184088 A1* | 6/2017 | Macari | F04B 43/1276 |

* cited by examiner

Fig.9

HOLDER FOR A CURVED DUCT PORTION

CROSS-REFERENCE TO RELATED APPLICATIONS

This application claims priority to IT Patent Application No. 102017000064361 filed on Jun. 9, 2017, and to PCT Application No. PCT/IB2018/054156 filed on Jun. 8, 2018, the entire contents of which are hereby incorporated by reference.

TECHNICAL FIELD

The present invention refers to a holder for a curved duct portion of a tube pump for extracorporeal blood circuits.

BACKGROUND ART

Typically, tube pumps are used as blood pumps or fluid replacement pumps in apparatuses for dialysis treatment and they are configured to pump a fluid by squeezing a curved tube by means of a rotor.

Before starting the dialysis treatment, technical operators, like nurses or doctors, have to perform some preliminary activities for preparing the device as, for example, connecting tubes to/from the tube pump through relative connectors.

In order to simplify these activities, a plurality of solutions has been proposed.

EP2397695 discloses a tube pump comprising a rotor to squeeze a curved portion of a duct. The duct is provided with a supply tube connected to an end of the curved portion via a supply-side connector and a discharge tube connected to the other end of the curved portion via a discharge-side connector.

A single-piece synthetic resin holder is connected with each one of said connectors. The holder is formed to have a size enabling outer peripheral surfaces of the connectors to be covered on the outside of the front surface of the dialysis apparatus. In this way, work for attaching/detaching the duct to/from the housing is easily performed. Also, since no fluid passage is provided in the holder itself, the configuration of the holder is simplified.

WO2005111424 discloses a roller pump consisting of a stator having a pump bed formed therein and a rotor for acting on a hose inserted into the pump bed in arcuate form, with the ends of the hose guided out of the pump bed crossing directly after exiting the pump bed. A pump segment thus results in the form of a Greek omega. The hoses can be guided further in a space-saving manner below or next to the roller pump due to this shape without there being any risk of kinking.

EP2682608 discloses a multi-connector incorporating a hose segment and intake and discharge lines of an extracorporeal blood circuit for mounting on a peristaltic pump of a medical device without tools. The multi-connector comprises a main body and two connector elements for respectively connecting the hose segment to the intake line and to the discharge line. The multi-connector is configured so that it can be mounted on the peristaltic pump in two positions, where a first position constitutes a treatment position and a second position constitutes a thread-out position for the extracorporeal blood circuit.

U.S. Pat. No. 6,494,692 discloses a peristaltic pump comprises a housing within which driving means in the form of a rotor having rollers mounted for rotation by a motor. A tube element is mounted in the housing and comprises a tube having end fittings. The body of the pump has two U-shaped recesses in each of which a groove is formed, where the groove are adapted to receive the flange formed on the respective end fittings. Flanges are oriented orthogonally with respect to the end fittings, so as the end fittings themselves when housed inside the pump are blocked and parallelly oriented the one another.

WO2005088132 discloses a roller pump comprising a rotor adapted to squeeze a curved portion of a duct. The duct at its ends comprises joint means arranged separately when the duct itself is inserted to the housing of the roller pump and when the latter is in operating condition.

US20140012176 discloses a multi-connector for extracorporeal blood treatment for applying a tube segment and the corresponding feeding and discharging lines to a roller pump. The multi-connector comprises two connector elements for connecting ends of the tube segment to the feeding line and to the discharge line respectively. The pump housing comprises a seat adapted to receive a first connector and which act as a fulcrum for allowing the multi-connector rotation. During the multi-connector rotation the reciprocal position of the connectors is fixed.

U.S. Pat. No. 4,545,744 discloses a roller pump comprising a stator member in which a pump bed is formed. In the interior of the pump bed a rotor is rotatably mounted. A pump hose can be inserted into the pump bed in a loop-like manner and its two ends are combined in immediate vicinity to each other in a connecting piece. The securing of the pump hose to the connecting piece is by means of hose clips or the like which compress, and thus secure, the pump hose.

DISCLOSURE OF THE INVENTION

The Applicant experienced that before using the tube pumps the latter are stored generally for a time comprised between 3 and 5 years. This long-time storage affects the physical conformation of the squeezable duct deforming it.

The Applicant has observed that, in all the prior art solutions proposed, the squeezable duct portion is stored according to a single predetermined radius of curvature. According to this configuration, the duct portion tends to be deformed resulting on a reduction of the diameter of at least a part of the duct portion with the consequence of a not accurate flow rate during the dialysis treatments.

The Applicant has thus faced the problem of avoiding deformation of the squeezable duct portion during long-time storage of tube pumps for the extracorporeal blood circuit.

The Applicant has found that an effective long time-storage without deforming the duct portion can be obtained by a holder comprising a supply-side connector and a discharge-side connector adapted to receive the curved duct portion which allows the connectors to move between a storage configuration, in which the supply-side connector is away to the discharge-side connector, and an operating configuration, in which the supply-side connector is close to said discharge-side connector.

Therefore, the present invention relates to a holder for a curved duct portion of a tube pump comprising a supply-side connector comprising a cavity for receiving an end of said curved duct portion, and a discharge-side connector comprising a cavity for receiving an other end of said curved duct portion, wherein said connectors are movable between a storage configuration, in which said supply-side connector is away to said discharge-side connector, and an operating configuration, in which said supply-side connector is close to said discharge-side connector.

According to a second aspect, the present invention relates to a tube pump comprising said holder.

BRIEF DESCRIPTION OF THE DRAWINGS

Other characteristics and advantages of the present invention will become better evident from the description of a preferred but not exclusive embodiment of a device for optical measurements, illustrated by way of an indicative, but not limitative example in the accompanying drawings in which.

WAYS OF CARRYING OUT THE INVENTION

A holder for a curved duct portion 8 of a tube pump according to the present invention is indicated with reference number 1 in the annexed figures.

Figure 9:
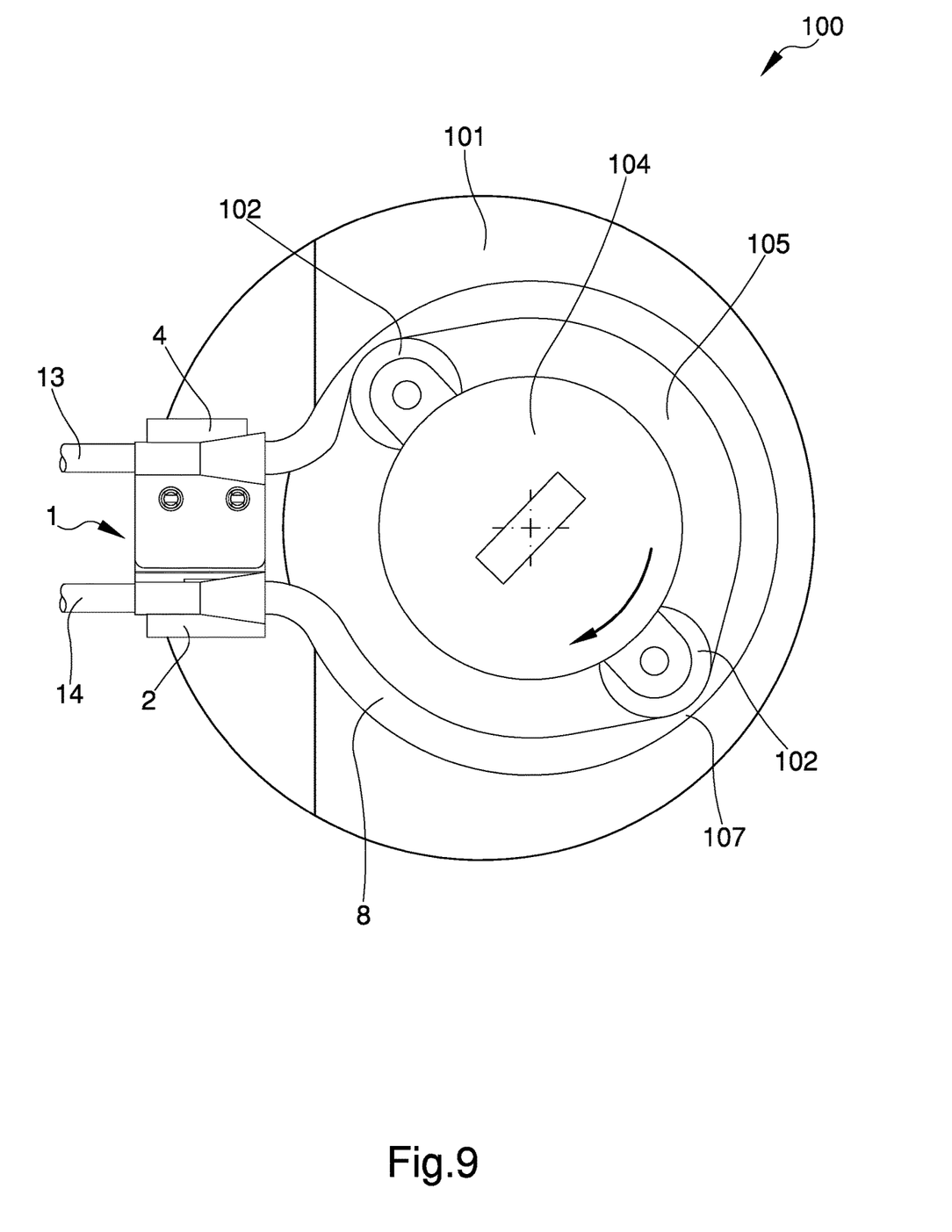
FIG. 9 is a perspective view of a pump including the holder of FIG. 1.

The tube pump is configured to pump a fluid (e.g. blood) by squeezing a curved duct portion 2 according to conventional methods, for example through rollers moved by a rotor 104 arranged on the body 101 of the pump 100. The body 101 comprises a supporting surface 105 on which the rotor 104 rotates. The supporting surface 105 has a substantially circular surface from which extends peripherally and orthogonally an internal part 107 for supporting the curved duct portion 8.

The holder 1 comprises a pair of connectors 2,4 for receiving the ends of a curved duct portion 8. In particular, the holder 1 comprises, a supply-side connector 2 having a cavity 3 for receiving an end of the curved duct portion 8 fitted therein and it comprises a discharge-side connector 4 having a cavity 5 for receiving another end of the curved duct portion 8 fitted therein.

Figure 1:
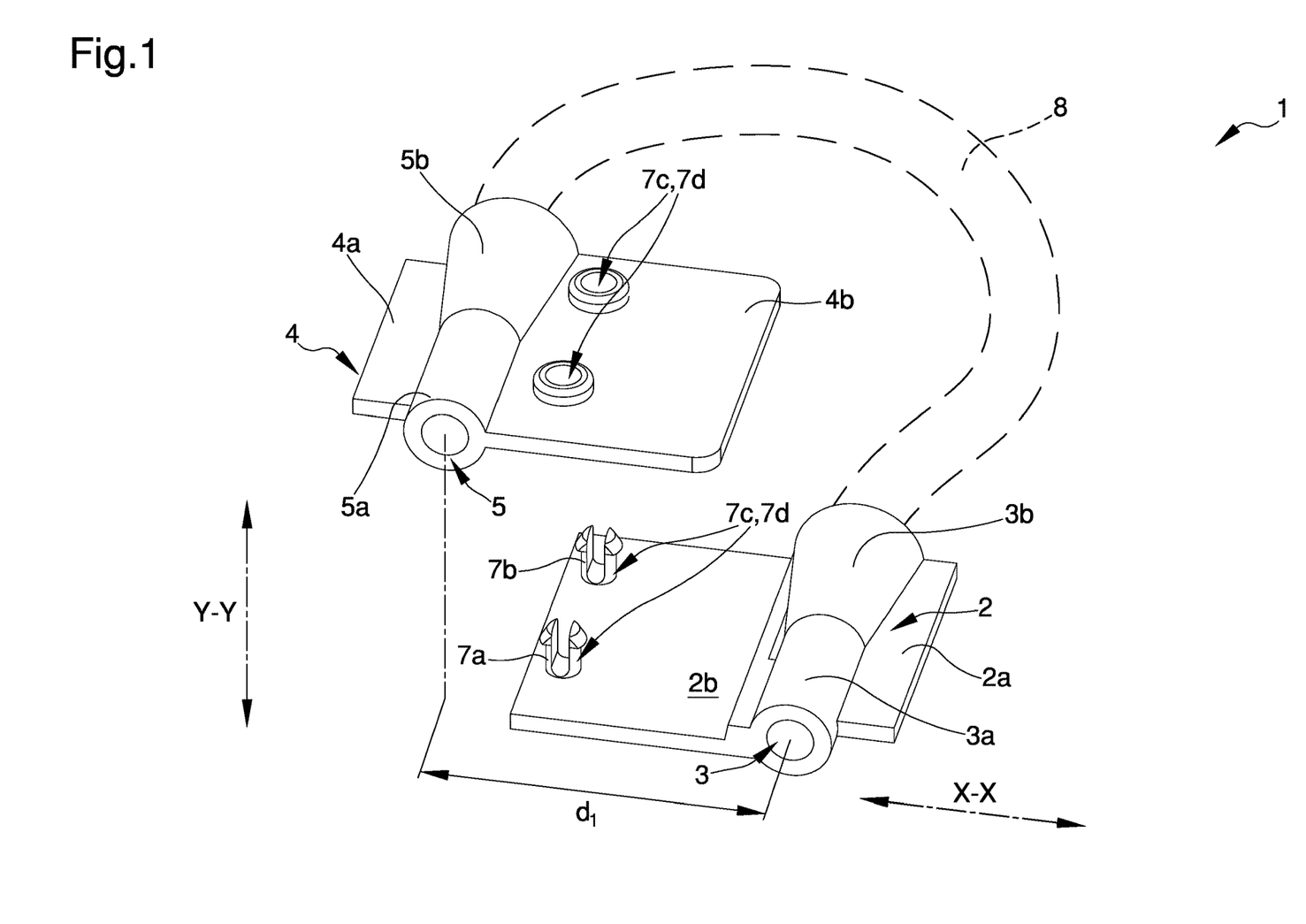
FIG. 1 is a perspective top view of a holder arranged in a storage configuration according to a first embodiment of the present invention.
Figure 2:
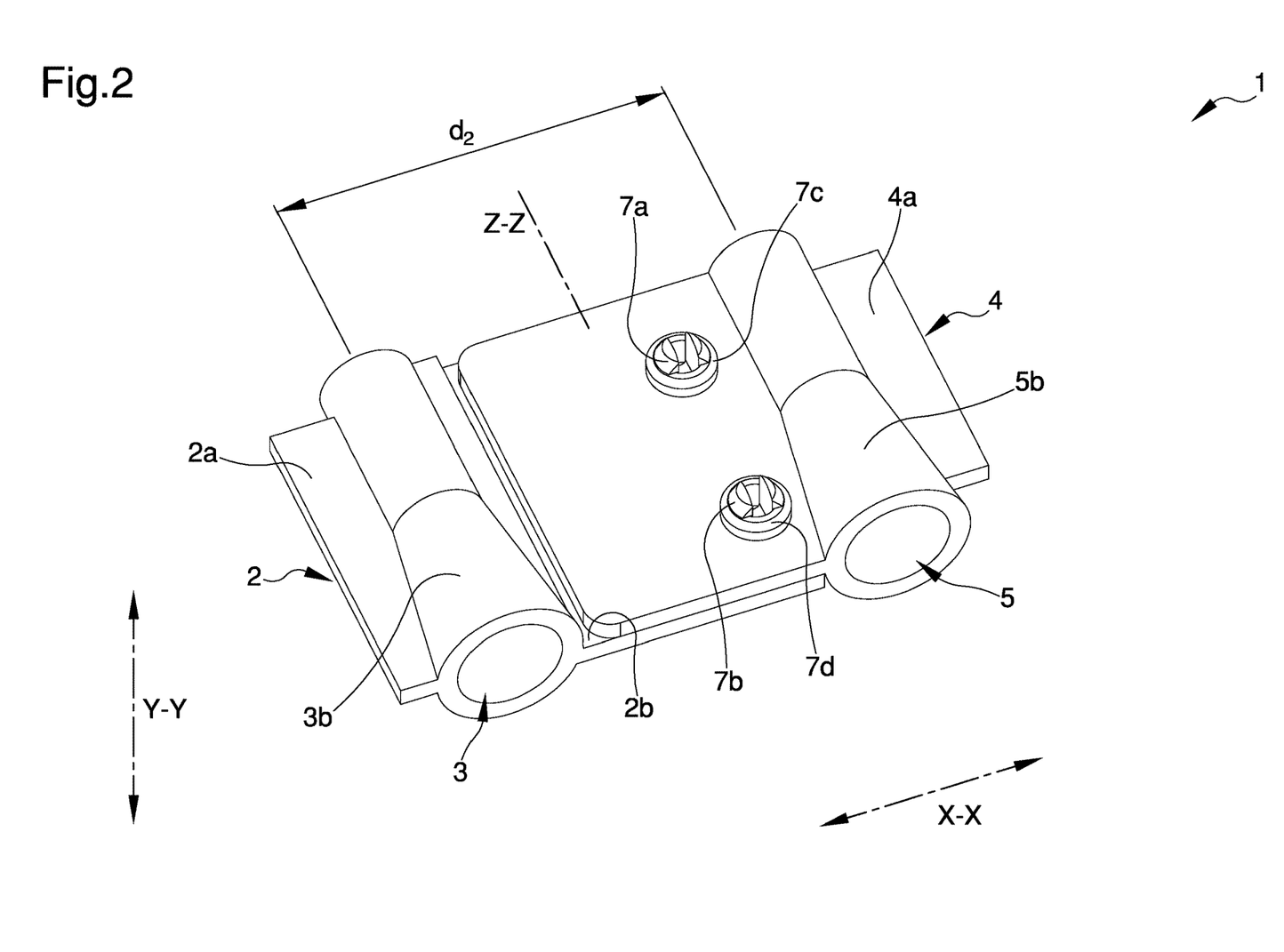
FIG. 2 is a perspective bottom view of the holder of FIG. 1 arranged in an operating configuration.

According to the first embodiment shown in the examples of FIGS. 1 and 2, the supply-side connector 2 has a preferably rectangular shape mainly extended for a predetermined length along a longitudinally direction X-X.

The cavity 3 is located substantially at the middle of the length of the supply-side connector 2. Similarly, the discharge-side connector 4 has a preferably rectangular shape where, substantially at the middle, is located the cavity 5. Preferably, the cavities 3,5 have circular section.

The supply-side connector 2 comprises a first plate 2a adapted to be connected to the pump 100 and a second plate 2b adapted to be removably connected to the discharge-side connector 4. Preferably, the first plate 2a is connected to the second plate 2b through the cavity 3. More preferably, first and second plate 2a, 2b are substantially coplanar extended. Similarly, the discharge-side connector 4 comprises a first plate 4a adapted to be connected to the pump 100 and a second plate 4b adapted to be removably connected to the discharge-side connector 4. Preferably, first and second plate 4a, 4b are substantially coplanar.

According to the invention, the connectors 2, 4 are movable the one with respect to the other between at least a storage configuration, in which the supply-side connector 2 is positioned away to the discharge-side connector 4, and an operating configuration, in which the supply-side connector 2 is close to the discharge-side connector 4 with respect to the storage configuration and in which the first plate 2a and the second plate 4b are engaged together substantially on a same plane X-Z.

According to a preferred embodiment, each cavity 3,5 comprises a first rectilinear tract 3a,5a adapted to receive at least partially an end of the curved duct portion 8 and second rectilinear tract 3b,5b adapted to receive at least partially a supply/discharge tube 13,14. In this way, the supply tube 13 is connected to an end of the curved duct portion 8 via the supply-side connector 2 and the discharge tube 14 is connected to an end of the curved duct portion 8 via the discharge-side connector 4.

Preferably, the second rectilinear tract 3b,5b of the cavity 3,5 is tapered towards the first rectilinear tract 3a,5a.

Preferably, the first rectilinear tract 3a,5a and the second rectilinear tract 3b,5b of the cavities 3,5 are coaxially extended.

Since the holder 1 comprises a pair of separate connectors 2,4, when the curved duct portion 8 is connected to the supply-side connector 2 and to the discharge-side connector 4 it acts as guiding means allowing the connectors 2,4 to move the one with respect to the other between the storage position and the operating position.

In the storage position (FIG. 1), the supply-side connector 2 is separated from the discharge-side connector 4 so that the connectors 2,4 (and hence their cavities 3,5) are positioned according to a predetermined configuration where the supply-side connector 2 is away from the discharge-side connector 4. In the operating position (FIG. 2), the supply-side connector 2 is connected to the discharge-side connector 4 so that the connectors 2,4 are positioned according to a predetermined configuration where the supply-side connector 2 is close to the discharge-side connector 4. In this way, the duct portion 8 can be stored in a storage configuration with a radius of curvature greater than the radius of curvature typically present when the pump is in operating configuration avoiding permanent deformation of the duct itself.

The curved duct portion 8 acting as a guiding means allowing the connectors 2,4 to move one towards each other so that, in the storage configuration, the cavities 3,5 are staggered and, in the operating configuration, the cavities 3,5 are parallelly aligned substantially on a same plane X-Z.

According to a preferred form of embodiments, the connectors 2,4 move one towards each other so that, in the storage configuration, the cavities 3,5 are staggered and, in the operating configuration, the cavities 3,5 are parallelly aligned substantially on a same plane X-Z.

With reference to the example shown in FIG. 1, the holder 1 comprises connecting means 7 adapted to act on said connectors 2,4 to prevent them from movements when the latters are in the operating configuration.

In particular, the supply-side connector 2 comprises two pins 7a,7b which project from the second plate 2b of the supply-side connector 2 along a direction Y-Y orthogonal to the longitudinal direction X-X.

The two pins 7a,7b are suitable to be inserted into corresponding mating recesses 7c,7d provided on the second plate 4b of the discharge-side connector 4.

Figure 3:
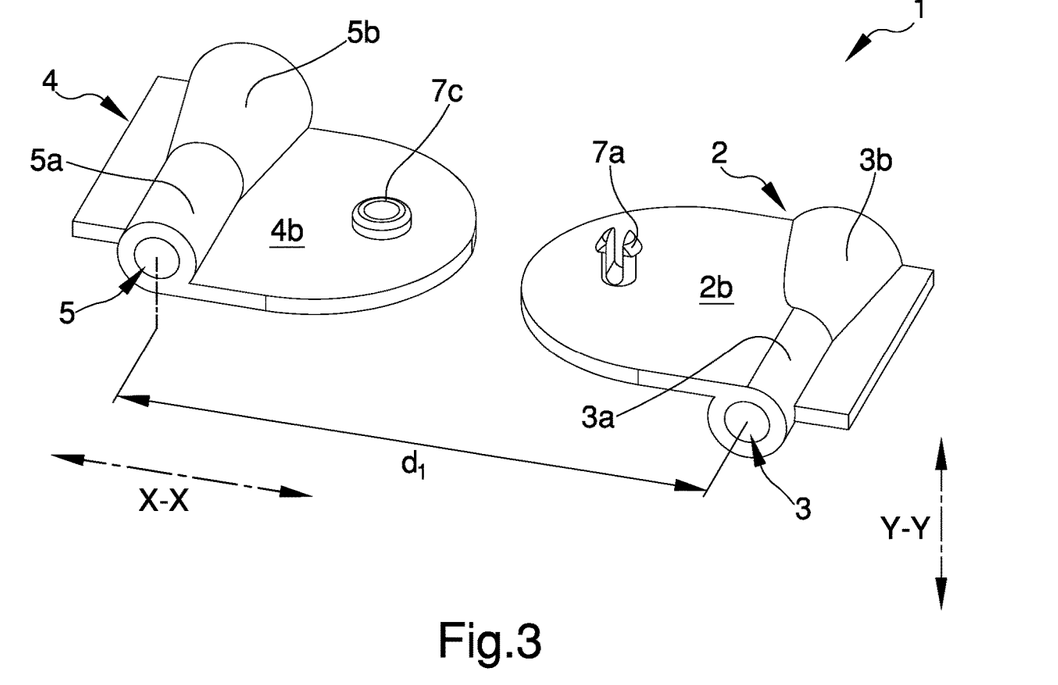
FIG. 3 is a perspective top view of the holder arranged in a storage configuration according to a variant of the first embodiment.
Figure 4:
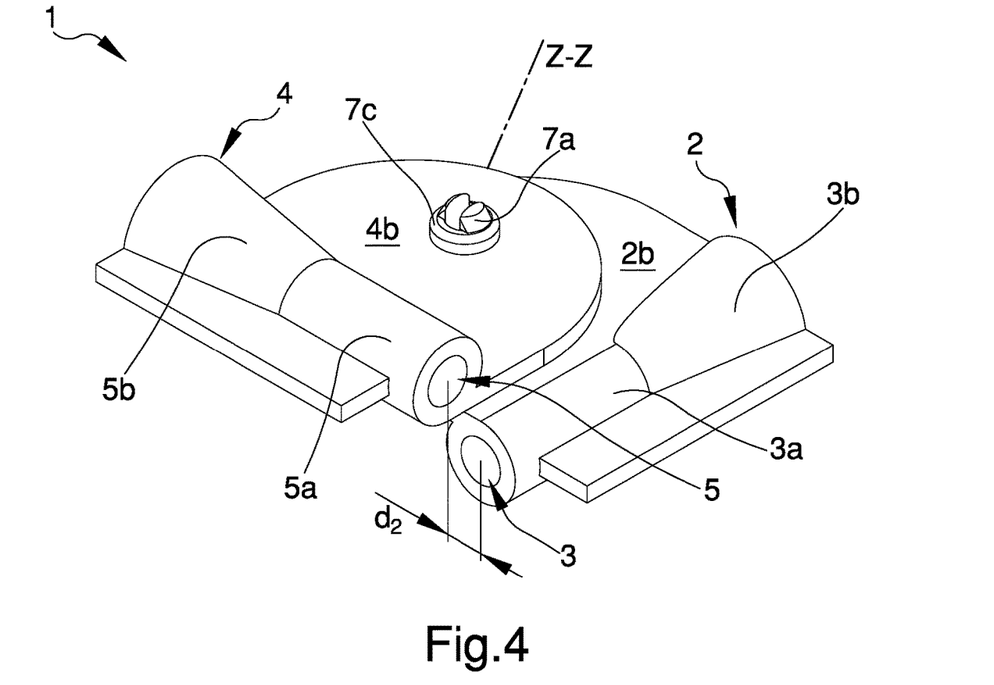
FIG. 4 is a perspective top view of the holder of FIG. 2 according to a variant of the first embodiment.

With reference to FIGS. 3 and 4, it is shown a variant of the first embodiment. In particular, the supply-side connector 2 and the discharge-side connector 4 comprise, respectively, only a plate 2a,2b each one acting as holder for the connectors 2,4. The plates 2b,4b are adapted for being removably connected one to each other and they have, preferably, semicircular shape.

The supply-side connector 2 comprises a pin 7a which project from the first plate 2b of the supply-side connector 2 and extends along its axis through direction Y-Y. The pin 7a is adapted to be inserted into corresponding mating recess 7c provided on the second plate 4b of the discharge-side connector 4.

As shown in the example of FIG. 3, in the storage configuration, the supply-side connector 2 is separated from discharge-side connector 4 so that connectors 2,4 (and hence cavities 3,5) be positioned according to a predetermined configuration wherein the supply-side connector 2 is away from discharge-side connector 4.

When the connectors are engaged as shown in FIG. 4, the discharge-side connector 4 may rotate with respect to the supply-side connector 2 around the axis of the pin 7a. In particular, connectors 2,4 are moveable between a storage configuration, in which cavities 3 are separated, and an operating configuration, in which connectors 2,4 rotate so that the first cavity 3 cross the second cavity 5.

Preferably, in the operating configuration, the first cavity 3 crosses the second cavity 5 at a substantially right angle.

Figure 5:
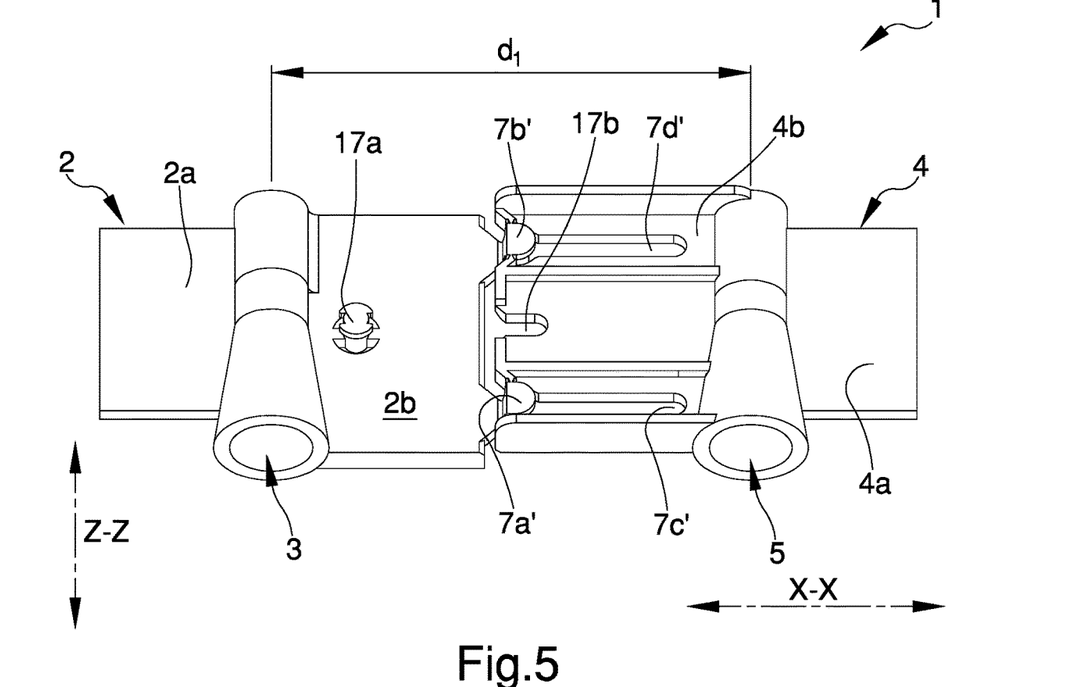
FIG. 5 is a perspective top view of a holder arranged in a storage configuration according to a second embodiment of the present invention.
Figure 6:
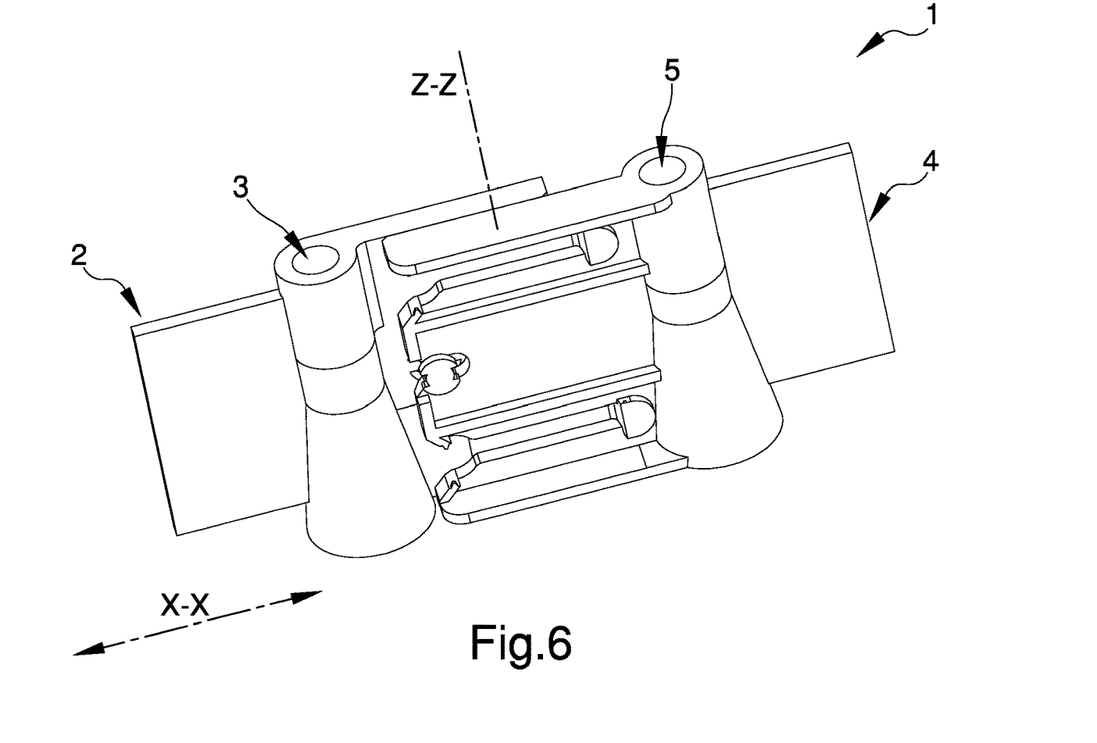
FIG. 6 is a perspective top view of the holder of FIG. 5 arranged in an operating configuration.

According to the second embodiment shown in the examples of FIGS. 5 and 6, recesses 7c',7d' formed on the second plate 4b of the discharge-side connector 2 have elongated ring-shape for receiving pins 7a',7b' projecting from the second plate 2b of the supply-side connector 2. In this way, the pins 7a',7b' and the recesses 7c',7d' act as guiding means allowing the connectors 2,4 to linearly move one towards each other along the longitudinal direction X-X so that, in both the storage and the operating configuration, the cavities 3,5 are parallel aligned on a substantially same plane X-Z.

With reference to the example shown in FIG. 5, the holder 1 comprises connecting means for removably coupling the supply-side connector 2 to the discharge-side connector 4. In particular, the connecting means act on said connectors 2,4 to prevent them from movements when the latters are in the operating configuration. In particular, the supply-side connector 2 comprises a pin 17a which projects from the second plate 2b of the supply-side connector 2 along a direction Y-Y orthogonal to the longitudinal direction X-X. The pin 17a is suitable to be inserted into a corresponding mating recess 17b provided on the second plate 4b of the discharge-side connector 4 after the linear movement from the storage configuration to the operating position is ended.

Figure 7:
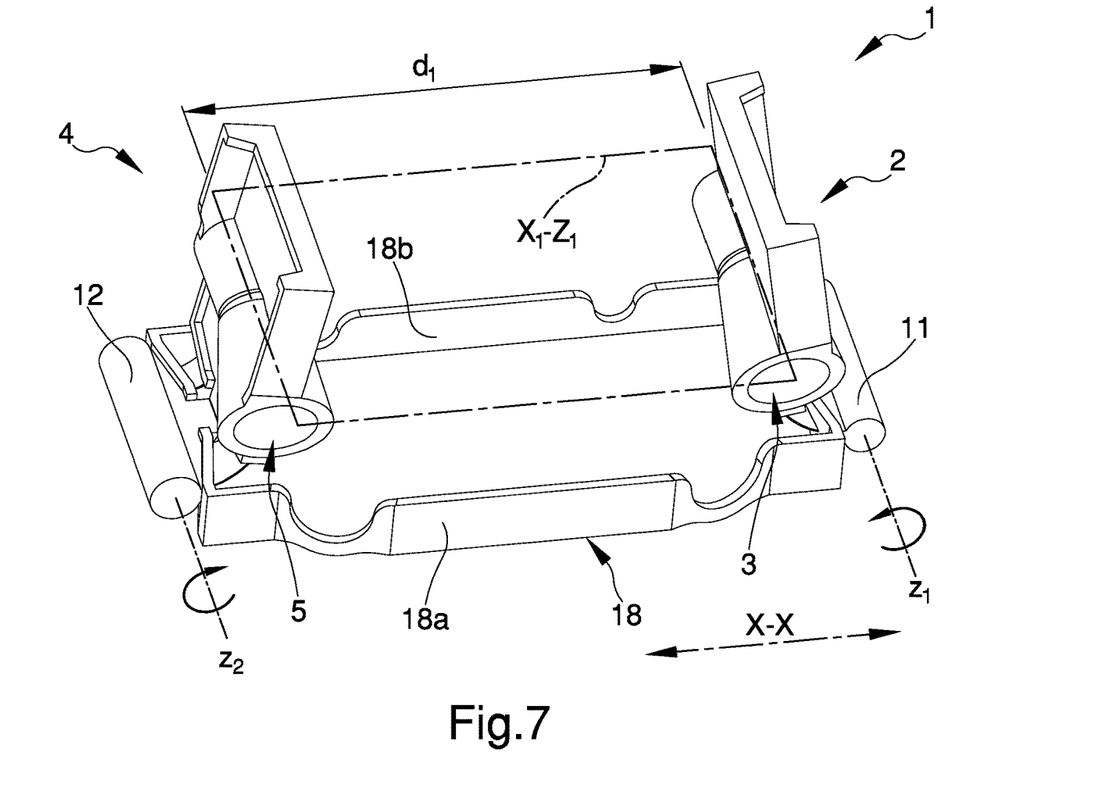
FIG. 7 is a perspective top view of the holder arranged in a storage configuration according to a third embodiment of the present invention.
Figure 8:
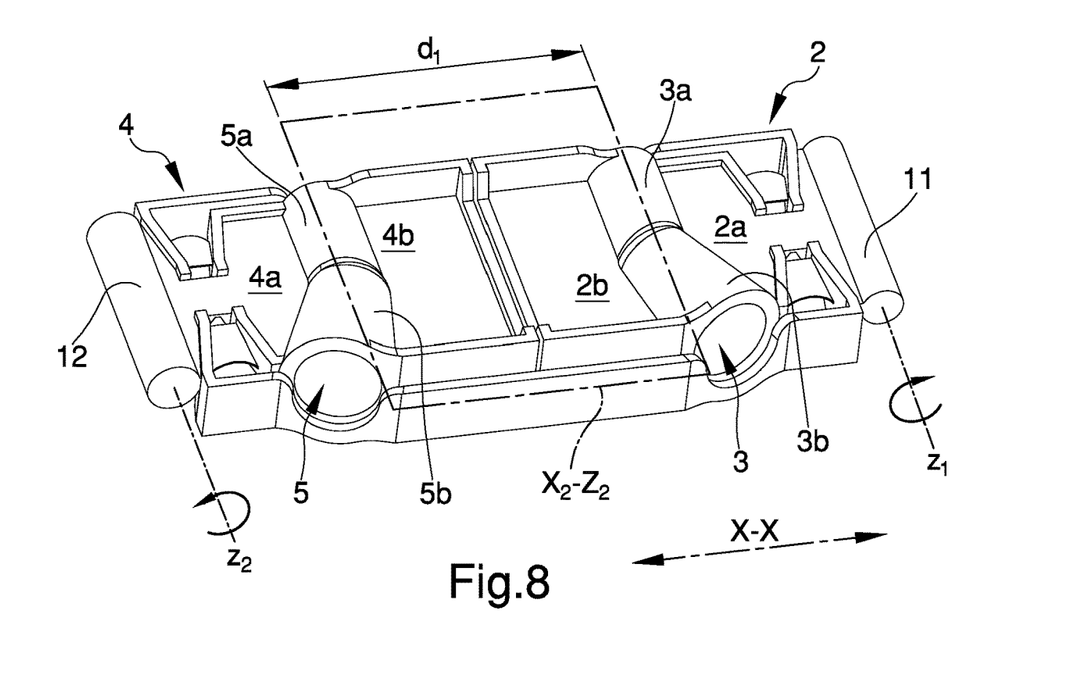
FIG. 8 is a perspective top view of the holder of FIG. 7 arranged in an operating configuration.

According to the third embodiment shown in the examples of FIGS. 7 and 8, the holder 1 comprises a pair of rotating means 11,12 acting on the connectors 2,4 for rotating them around parallelly rotating axes $z_1, z_2$. In this way, the connectors 2,4 are rotatably moved one towards the other so that, in the storage configuration (FIG. 7), the cavities 3,5 be substantially parallelly aligned on a first plane $X_1-Z_1$ and, in the operating configuration (FIG. 8), the cavities 3,5 are substantially aligned on a second plane $X_2-Z_2$ parallel to the first plane $X_1-Z_1$. In particular, in the storage configuration, the cavities are rotated with respect to the operating configuration.

Preferably, the connectors 2,4 can rotate individually around the rotation axes $z_1, z_2$ between the storage configuration, wherein the first cavity 3 is positioned away from the second cavity 5, and the operating configuration, in which the first cavity 3 is close to the second cavity 5.

According to the embodiment shown in the example of FIG. 8, the first tract 3b,5b of the cavities 3,5 is slightly offset with respect to the second tract 3a,5a. In particular, the orientation of the first tract 3b,5b is staggered by an angle comprised between 10° and 50°, preferably an angle of 30°, with respect to the second tract 3a,5a.

As shown in the example of FIG. 7, the holder 1 comprises a frame 18 for supporting the rotating means 11,12. The frame 18 comprises two parallel bars 18a,18b extended along the longitudinal direction X-X where, at their ends, the rotating means 11,12 are coupled.

Preferably, the frame 18 and the rotating means 11,12 is a one-piece molding.

Preferably, each rotating means 11,12 comprise a hinge formed, respectively, at the end of the first plate 2a of the supply-side connector 2 and at the end of the first plate 4a of the discharge-side connector 4.

Preferably, the connectors are made of one-piece of rigid type material, for example, of PETG (Polyethylene Terephthalate-Glycol) or PVC; of course, other rigid plastics materials can alternatively be used.

According to a preferred embodiment, when the connectors are in the storage configuration, the cavities 3,5, if the connectors are not engaged together, are free to remain at a distance that may be at most the total length of the pump. If the connectors are engaged together, the cavities 3,5 are separated one from each other by a distance d1 which depends on the geometry of the holder when in the operating configuration, and which is a multiple of $d_2$.

When the connectors are in the operating configuration, their cavities 3,5 are separate each other of a distance dz which depends form the length and from the configuration of the pump. In this way, the duct portion 8 can be stored with a radius of curvature greater than the radius of curvature typically present in the operating configuration avoiding permanent deformation of the squeezable duct portion and, at the same time, maintaining an accurate flow rate of the pump during dialysis treatments.

The invention claimed is:

1. A holder for a curved duct portion of a tube pump, the holder comprising:
   a supply-side connector comprising a first cavity and a first place connected together, said first cavity being adapted for receiving an end of said curved duct portion, and
   a discharge-side connector comprising a second cavity and a second plate connected together, said second cavity being adapted for receiving another end of said curved duct portion, wherein
   said connectors are movable the one with respect to the other between a storage configuration and an operating configuration, in which said supply-side connector is positioned away to said discharge-side connector, and an operating configuration, in which said supply-side connector is close to said discharge-side connector and in which said first and second plate are engaged together substantially on a same plane, and said connectors are linearly movable one towards each other so that, in both said storage and said operating configuration, said cavities are parallel on a same plane.

* * * * *